United States Patent
Merrill et al.

(10) Patent No.: US 6,897,346 B1
(45) Date of Patent: May 24, 2005

(54) AROMATIC CONVERSION PROCESS EMPLOYING LOW SURFACE AREA ZEOLITE Y

(75) Inventors: James T. Merrill, Katy, TX (US); James R. Butler, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/329,502

(22) Filed: Jun. 10, 1999

(51) Int. Cl.$^7$ ............................................. C07C 2/66
(52) U.S. Cl. ................ 585/323; 585/475; 585/467
(58) Field of Search ..................... 585/479, 467, 585/449, 321; 502/79

(56) References Cited

U.S. PATENT DOCUMENTS

| | | | |
|---|---|---|---|
| 4,169,111 A | 9/1979 | Wight | 585/325 |
| 4,185,040 A | 1/1980 | Ward | 585/407 |
| 4,459,426 A | 7/1984 | Inwood et al. | 585/323 |
| 4,774,377 A | 9/1988 | Barger et al. | 585/323 |
| 5,324,877 A * | 6/1994 | West et al. | 585/467 |
| 5,900,518 A | 5/1999 | Merrill et al. | 585/323 |
| 5,955,642 A * | 9/1999 | Merrill et al. | 585/323 |

FOREIGN PATENT DOCUMENTS

| | | |
|---|---|---|
| EP | 0467007 | 1/1992 |
| EP | 457007 | 4/1996 |

* cited by examiner

Primary Examiner—Thuan D Dang
(74) Attorney, Agent, or Firm—William D. Jackson

(57) ABSTRACT

A process for the transalkylation of polyalkylated aromatic compounds over a high porosity zeolite-Y molecular sieve having a surface area of no more than 500 m$^2$/g. A feedstock comprising a polyalkylated aromatic component, including polyalkylbenzenes in which the predominant alkyl substituents contain from 2 to 4 carbon atoms, is supplied to a transalkylation reaction zone containing the high porosity zeolite-Y catalyst. Benzene is also supplied to the transalkylation zone, and the reaction zone is operated under temperature and pressure conditions to maintain the polyalkylated aromatic component in the liquid phase and which are effective to cause disproportionation of the polyalkylated aromatic component to arrive a disproportionation product having a reduced polyalkylbenzene content and an enhanced monoalkylbenzene content. An alkylation reaction zone is provided which contains a molecular sieve aromatic alkylation catalyst having an average pore size which is less than the average pore size of the average pore size of the high porosity zeolite-Y. A feedstock comprising benzene in a $C_2$–$C_4$ alkylating agent is supplied to the alkylation reaction zone which is operated under conditions to produce alkylation of the benzene by the alkylating agent in the presence of the molecular sieve alkylation catalyst. The alkylation product from the alkylation reaction zone is supplied to an intermediate recovery zone for the separation and recovery of a monoalkylbenzene, e.g. ethylbenzene, from the alkylation product; together with the recovery of a polyalkylated aromatic component employing a dialkylbenzene, e.g. diethylbenzene. The polyalkylated aromatic component is employed in at least a portion of the feedstream supplied to the transalkylation reactor.

4 Claims, 4 Drawing Sheets

AROMATIC CONVERSION PROCESS EMPLOYING LOW SURFACE AREA ZEOLITE Y

FIELD OF THE INVENTION

This invention involves the transalkylation of aromatic compounds over a high porosity zeolite-Y molecular sieve and such transalkylation in combination with alkylation of an aromatic substrate such as benzene over a silicalite aromatic alkylation catalyst having an average pore size less than that of the zeolite-Y catalyst.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Transalkylation reactors are normally employed in an integrated process which involves an initial alkylation of the aromatic substrate followed by an intermediate recovery operation and then transalkylation. Typically, an alkylation reactor which produces a mixture of mono- and poly-alkyl benzenes is coupled through several separation stages to the downstream transalkylation reactor. Transalkylation may, in turn, be followed by separation and/or recycle procedures. Such alkylation and transalkylation conversion processes can be carried out in the liquid phase, in the vapor phase, or under conditions in which both liquid and vapor phases are present.

In both alkylation and transalkylation, whether conducted in the liquid phase or in the vapor phase, it is a conventional practice to employ catalysts in the reactors comprising shape-selective molecular sieves. The molecular sieves may be the sane or different for the alkylation and transalkylation reactions and, in fact, accompanying side reactions in many alkylation reactors involves transalkylation. Thus, alkylation and transalkylation reactions may occur simultaneously within a single reactor. This can be characterized in terms of the operation of a plurality of series-connected catalyst beds in an alkylation reactor. For example, where various series-connected catalyst beds are employed in an alkylation reactor as described below, it is a conventional practice to employ interstage injection between the catalyst beds, which tends to enhance transalkylation reactions within the alkylation reactor. For example, in the ethylation of benzene with ethylene to produce ethylbenzene, the alkylation product within the reactor includes not only ethylbenzene but also polyethylbenzene, principally diethylbenzene with reduced amounts of triethylbenzene, as well as other alkylated aromatics such as cumene and butylbenzene. The interstage injection of the ethylene results not only further in alkylation reactions but also transalkylation reactions where, for example, benzene and diethylbenzene undergo transalkylation to produce ethylbenzene. Thus, even though a separate transalkylation reactor is connected downstream through a series of separation stages, it is an accepted practice to minimize polyalkylation within the alkylation reactor in order to facilitate the subsequent treatment and separation steps.

As noted above, the molecular sieves employed in the separate alkylation and transalkylation reactors can be the same or different. As described below, employ a relatively small to intermediate pore size molecular sieve such as ZSM-5, ZSM-11, or silicalite in the alkylation reactor and follow this with a molecular sieve having a somewhat larger pore size, such as zeolite-Y, zeolite-$\Omega$, or mordenite. However, as indicated by the following discussion, this procedure is by no means universally followed.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

The molecular sieve silicalite referred to above is a well-known alkylation catalyst. For example, U.S. Pat. No. 4,520,220 to Watson et al discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al, the alkylation procedure can be carried out in a multi-bed alkylation reactor at temperatures ranging from about 350°–500° C. and, more desirably, about 400°14 475° C., with or without a steam co-feed. The reactor conditions in Watson et al are such as to provide generally for vapor phase alkylation conditions.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al, silicalite is employed as a catalyst in the alkylation of a monoalkylated substrate, toluene or ethylbenzene, in order to produce the corresponding dialkylbenzene, such as ethyl toluene or diethylbenzene. Specifically disclosed in Butler et al is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

Another example involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperature generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The Na$_2$O content of the zeolite should be less than 0.5 wt. %. Examples of suitable zeolites include molecular sieves of the X, Y, L, B, ZSM-5, and omega crystal types, with steam stabilized hydrogen zeolite being preferred. Specifically disclosed is a steam stabilized ammonium Y zeolite containing about 0.2% Na$_2$O. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al states that rapid catalyst deactivation occurs under most alkylating conditions when no liquid phase is present.

U.S. Pat. No. 4,169,111 to Ward et al discloses an alkylation/transalkylation process for the manufacture of ethylbenzene employing crystalline aluminosilicates in the alklylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5 and omega crystal types with steam stabilized Y zeolite containing about 0.2% Na$_2$O being preferred. The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-β, zeolite-Y or zeolite-Ω or in the vapor phase employing a catalyst such as silicalite or ZSM-5. In the Butler process where vapor phase alkylation is followed by liquid phase transalkylation, substantial quantities of water may be included in the feedstream to the alkylation reactor. In this case, the feed to the transalkylation reactor may be dehydrated to lower the water content. The transalkylation catalyst may take the form of a zeolite-Y or zeolite-Ω.

SUMMARY OF THE INVENTION

In accordance with the present invention, there is provided a process for the transalkylation of polyalkylated aromatic compounds over a high porosity zeolite-Y molecular sieve. The high porosity zeolite-Y catalyst is characterized as having a surface area of no more than 500 m$^2$/g, as contrasted with a surface area of standard zeolite-Y catalysts ranging from more than 600 m$^2$/g to as much as 700–800 m$^2$/g. As will be recognized by those skilled in the art, the surface area of a molecular sieve catalyst provides an inverse measurement of its porosity; that is, surface area is inversely proportionate to its porosity. In carrying out the invention, a feedstock comprising a polyalkylated aromatic component, including polyalkylbenzenes in which the predominant alkyl substituents contain from 2 to 4 carbon atoms, is supplied to a transalkylation reaction zone containing the high porosity zeolite-Y catalyst. Benzene is also supplied to the transalkylation zone, and the reaction zone is operated under temperature and pressure conditions to maintain the polyalkylated aromatic component in the liquid phase and which are effective to cause disproportionation of the polyalkylated aromatic component to arrive a disproportionation product having a reduced polyalkylbenzene content in an enhanced monoalkylbenzene content. Preferably, the high porosity zeolite-Y molecular sieve used in the reaction zone has a surface area of about 400 m$^2$/g or less and, more specifically, a surface area within the range of about 350–400 m$^2$/g. Preferably, the polyalkylated benzene comprises alkyl substituents containing 2 or 3 carbon atoms, and more specifically, the polyalkylated aromatic component comprises polyethylbenzene.

In a further aspect of the invention, there is provided an alkylation reaction zone which contains a molecular sieve aromatic alkylation catalyst having an average pore size which is less than the average pore size of the average pore size of the high porosity zeolite-Y. A feedstock comprising benzene in a $C_2$–$C_4$ alkylating agent is supplied to the alkylation reaction zone which is operated under conditions to produce alkylation of the benzene by the alkylating agent in the presence of the molecular sieve alkylation catalyst. The resultant alkylated product comprises a mixture of monoalkylated and polyalkylated aromatic components. The alkylation product from the alkylation reaction zone is supplied to an intermediate recovery zone for the separation and recovery of a monoalkylbenzene, e.g. ethylbenzene, from the alkylation product, together with the recovery of a polyalkylated aromatic component employing a dialkylbenzene, e.g. diethylbenzene. The polyalkylated aromatic component is employed in at least a portion of the feedstream supplied to the transalkylation reactor.

DETAILED DESCRIPTION OF THE INVENTION

Figure 1:
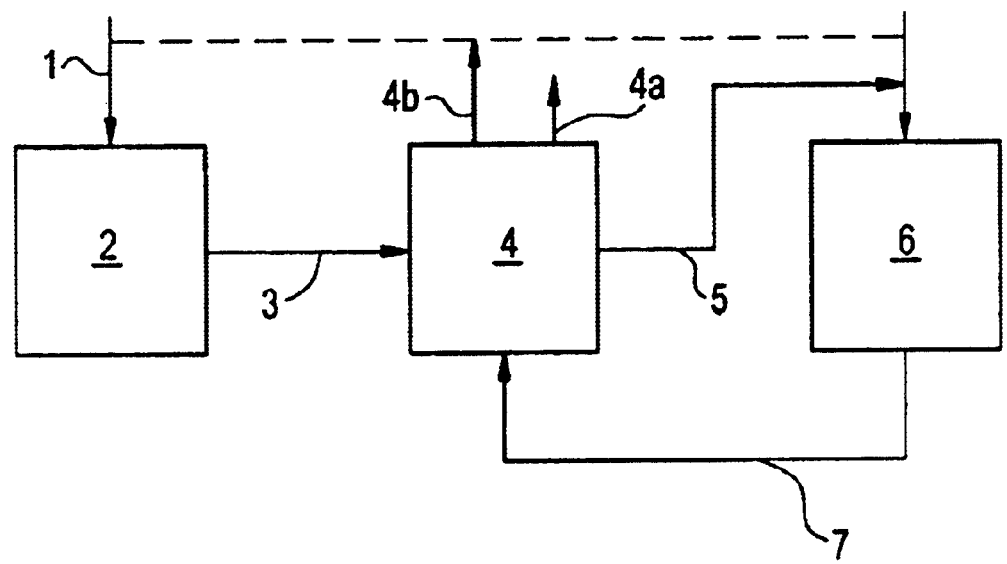
FIG. 1 is an idealized schematic block diagram of an alkylation/transalkylation process carried out in accordance with the present invention.

A preferred embodiment of the present invention involves vapor phase alkylation of an aromatic substrate comprising benzene in a multistage reaction zone followed by liquid phase transalkylation in which the alkylation and transalkylation reactors are integrated with intermediate separation zones in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The alkylation reactor is a multistage reaction zone containing at least three series connected catalyst beds which contain a pentasil molecular sieve aromatic alkylation catalyst, preferably a silicalite alkylation catalyst. As described in greater detail below, the silicalite alkylation catalyst preferably is silicalite characterized as having a high monoclinicity and a small sodium content. The catalyst used in the transalkylation reactor is a high porosity zeolite-Y having the characteristics described above. The alkylation reactor is normally operated at substantially higher temperature conditions than the transalkylation reactor, and if desired, the recycled output from the transalkylation reactor is passed in a heat exchange relationship with the alkylation reactor product feed to the initial benzene separation zone.

A further aspect of the invention involves a multistage alkylation reactor with the output coupled to a four-stage separation system which in turn supplies a polyethylbenzene feed to a transalkylation reactor. In the embodiment of the invention described herein, parallel alkylation and transalkylation reactors are employed so that simultaneous catalyst regeneration can occur during operation of the alkylation and transalkylation reactions. Preferably the alkylation reactor comprises at least four catalyst beds. More beds can be provided, and it will sometimes be advantageous to provide at least five catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

As Normally in the operation of multi-stage reaction zone of the type involved in the present invention, benzene and ethylene (or other alkylating agent) is introduced as a mixture to the first catalyst bed at the top of the reaction zone and also in between the several successive stages of if catalyst beds. In the present invention, ethylene is supplied along with benzene to the top of the catalyst bed top of the reactor. In addition, interstage injection of ethylene and benzene is provided for between the subsequent catalyst beds. The benzene to ethylene mole ratio is about 18 as injected into the top of the alkylation reactor and progressively decreases because of the interstage injection of ethylene and of course the alkylation of the benzene to ethyl benzene and polyethylbenzenes.

The preferred silicalite alkylation catalyst employed in the integrated process of the present invention does not require the presence of water to stabilize the catalyst, so a water or steam co-feed, as is sometimes used in connection with silicalite, is not called for in this invention. Interstage injection of ethylene is normally employed. The interstage injection of the benzene or other aromatic substrate can also be provided for. The mole ratio of the aromatic substrate to the ethylene at the interstage injection points can vary from zero (no benzene injection) up to about five. The benzene in many cases will be employed in an amount less than the amount of ethylene on a mole basis. Stated otherwise, benzene can either not be injected between the catalyst beds or, if injected, can be employed in a relatively minor amount, i.e., a mole ratio of benzene to ethylene of less than one. On the other hand, the mole ratio of the aromatic substrate to the alkylating agent can be as high as five. This is coupled with a somewhat lower operating temperature than would normally be the case for vapor phase alkylation. In the preferred embodiment of the invention, the temperature of the benzene stream into the top of the alkylation reactor will be in the order of 720° F. or lower. The alkylation reaction is, of course, an exothermic reaction so that the temperature will be increased progressively throughout the alkylation column as noted previously.

The zeolite-Y transalkylation catalyst employed in the present invention is topologically similar to standard zeolite-Y in terms of crystal structure faujasite and silica/alumina ratio. The zeolite-Y should have a silica/alumina atomic ratio within the range of 2–5 and such catalysts are normally characterized as being intermediate silica/alumina ratio zeolites. Zeolite-Y in the hydrogen form exhibits a pore size of about 7 and a surface area which is usually in excess of about 600 m$^2$/g and is usually in the range of about 700–800 m$^2$/g. Zeolite-Y typically has a crystallite size of about one micron and a unit cell size of about 24.5 Angstroms. The high porosity zeolite-Y used in the present invention has a substantially lower surface area, indicative of a somewhat larger pore size, greater than 7 and ranging up to about 8 Angstroms (Å) and a bulk density which is about 10–20% less than the bulk density of normal zeolite-Y.

The foregoing catalyst characteristics are for the zeolite-Y catalyst as it exists in the crystallite form. Normally, the zeolite-Y catalyst, as in the case of other molecular sieve catalysts, will be mulled with a binder such as silica or alumina and extruded to catalyst particles. The catalyst may be used in the form of cylindrical extrudates, typically of $\frac{1}{16}$ to $\frac{1}{8}$ inch in diameter or in the nature of trilobal shapes as described in the aforementioned U.S. Pat. No. 4,185,040 to Ward et al. As contrasted with the silicalite alkylation catalyst described below, the high porosity zeolite-Y has a larger pore size and also a larger crystal size.

The preferred alkylation catalyst is a molecular sieve from the pentasil family of high silica molecular sieves or zeolites. Such pentasil molecular sieves are described, for example, in Kokotailo et al, "Pentasil Family of High Silica Crystalline Materials," Chem. Soc. Special Publ. 33, 133–139 (1980). These molecular sieves pentasils can include high silica alumina ratio ZSM-5, such as described, for example, in Wu et al, "ZSM-5-Type Materials. Factors Affecting Crystal Symmetry," *The Journal of Physical Chemistry*, Vol. 83, No. 21, 1979, or silicalite molecular sieves, as described, for example, in Gourgue et al, "Physico-chemical characterization of pentasil type materials, I. Precursors and calcined zeolites," *Zeolites*, 1985, Vol. 5, November, and Gourgue et al, "Physico-chemical characterization of pentasil type materials, II. Thermal analysis of the precursors, Zeolites, 1985, Vol 5, November.

The silicalite or other pentasil molecular sieve alkylation catalyst has a somewhat smaller pore size than the high porosity zeolite-Y employed in the transalkylation reactor. The preferred silicalite catalyst has a somewhat smaller crystal size than is usually the case. Preferably, the crystal size is about 0.5$\mu$, or even somewhat smaller, as contrasted with a crystal sizes of perhaps 1–2$\mu$ for similar catalysts.

A preferred silicalite for use with high porosity zeolite-Y in the present invention is extruded with an alumina binder in a "trilobe" shape having a nominal diameter of about $\frac{1}{16}$" and a length of the extrudate of about $\frac{1}{8}$–$\frac{1}{4}$". The "trilobe" cross sectional shape is something on the order of a three leaf clover. The purpose of this shape is to increase the surface area of the extruded catalyst beyond what one would expect with a normal cylindrical extrudate. The preferred silicalite catalyst is characterized as monoclinic silicalite. Monoclinic silicalite may be prepared as disclosed in U.S. Pat. No. 4,781,906 to Cahen et al and U.S. Pat. No. 4,772,456 to DeClippeleir et al. Preferably the catalysts will have near 100% monoclinicity) although silicalite catalysts that are 70–80% monoclinic and about 20–30% orthorhombic symmetry may be used in the preferred embodiment of the invention. The silicalite preferably is present in an amount of 75–80 wt. % with the alumina binder being present in an amount of 20–25 wt. %. The silica/alumina ratio of the preferred silicalite is about 200, or more normally, 225. The silicalite may have an alpha value of about 20–30. The "alpha value" is characterized in terms of the activity of a catalyst for tracking hexane as disclosed in U.S. Pat. No. 4,284,529 to Shihabi and U.S. Pat. No. 4,559,314 to Shihabi. The catalyst contains small amounts of sodium and iron.

The preferred silicalite catalyst has a crystal structure characterized by an aluminum rich outer shell and an aluminum deficient interior portion when compared with the outer shell. The silicalite catalyst is dry and has no appreciable or intended water content. The alumni binder is a high purity alumina such as "catapal alumina." The silicalite catalyst preferably contains only a small amount of sodium, about 70–200 ppm sodium oxide, and contains only a small amount of iron oxide, about 300–600 ppm. The catalyst need not contain any additional "promoter" metals incorporated during the synthesis of the catalyst.

As noted above, the silicalite alkylation catalyst, like the high porosity zeolite-Y, preferably is extruded with a binder, such as an alumina binder, in an amount of about 20 wt. %. The preferred binder is one providing a relatively large pore size, not to be confused with the pore size of the zeolite itself, of about 1,000–1,800 angstroms. The average pore size as determined by the binder may range up to as high as about 4,000 angstroms. The silicalite alkylation catalysts will normally have a silica/alumina ratio of about 220 to 320 and is of predominantly monoclinic symmetry.

Turning now to the drawings and referring first to FIG. 1, there is illustrated a schematic block diagram of an alkylation/transalkylation process carried out in accordance with the present invention. As shown in FIG. 1, a product stream comprising a mixture of ethylene and benzene in a GNU mole ratio of benzene to ethylene about 5 to 20 supplied via line 1 to an alkylation zone 2. Alkylation zone 2 comprises one or more multi-stages reactor having a plurality of series-connected catalyst beds containing the preferred high silica/alumina ratio silicalite as described in greater detail below. The alkylation zone is operated at temperature and pressure conditions to maintain the alkylation reaction in the vapor phase, i.e. the aromatic substrate is in the vapor phase, and at a feed rate to provide a space velocity enhancing diethylbenzene production while retarding xylene production.

The output from the alkylation reactor is supplied via line 3 to an intermediate recovery zone 4 which provides for the separation and recovery of ethylbenzene as a product. Thus, ethylbenzene is withdrawn from zone 4 via line 4a and applied for any suitable purposes such as in the production of vinylbenzene. Recovery zone 4 normally will be characterized by a plurality of series-connected distillation columns as described below and will result in a heavy polyalkylated product stream which is supplied via line 5 to a transalkylation zone 6. Typically, benzene will also be recovered from the intermediate recovery zone via a line 4b. The benzene may be applied as indicated by the broken lines both for recycle back to the alkylation reactor and also to the transalkylation zone as may be appropriate. Within the transalkylation zone, the benzene and diethylbenzene undergo a disproportionation reaction resulting in a product of enhanced ethylbenzene content and diminished benzene and diethylbenzene content. Typically, at least part of the output from the transalkylation zone will be supplied via line 7 for recycle to the separation zone 4.

Figure 2:
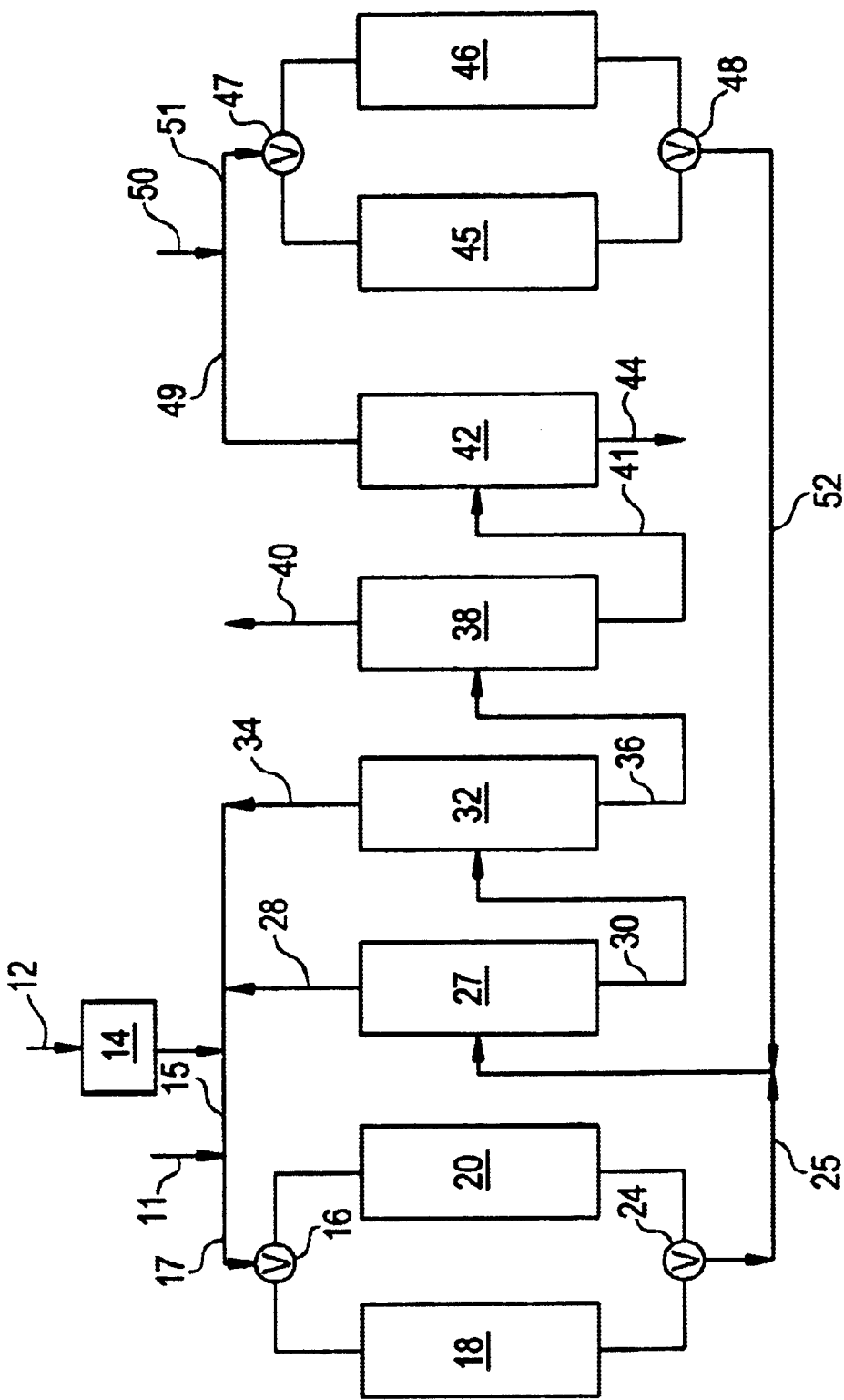
FIG. 2 is a schematic illustration of a process embodying the present invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the integrated alkylation/transalkylation process. As shown in FIG. 2, an input feed stream is supplied by fresh ethylene through line 11 and fresh benzene through line 12. Line 12 is provided with a preheater 14 to heat the benzene stream to the desired temperature for the alkylation reaction. The feedstream is applied through a two-way, three-position valve 16 and inlet line 17 to the top of an alkylation reaction zone 18 which comprises a plurality of series connected catalyst beds each of which contains a silicalite alkylation catalyst. The reactor is operated at an average temperature, preferably within the range of 700° F.–800° F. and at pressure conditions of about 200 to 350 psia, to maintain the benzene in the gaseous phase.

Figure 3:
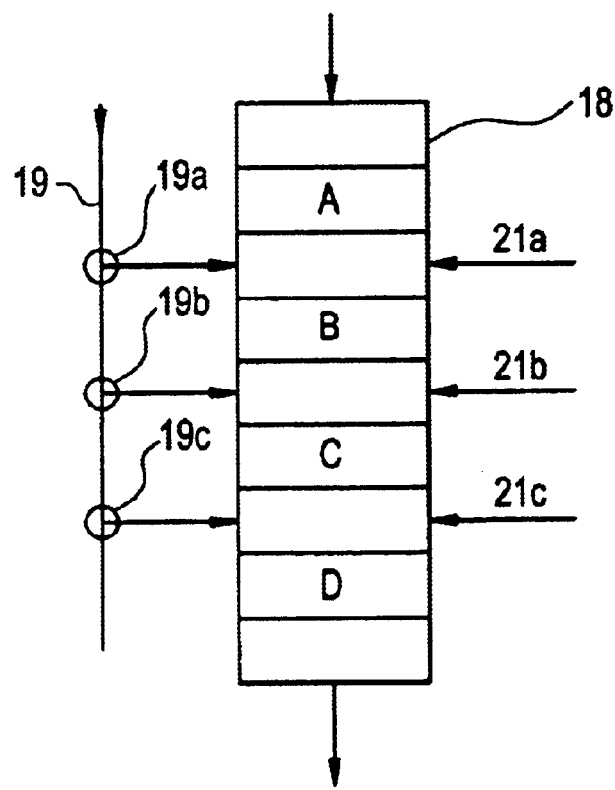
FIG. 3 is a schematic illustration of an alkylation reaction comprising a plurality of series-connected catalyst beds with the interstage injection of feed components.

A second reaction zone 20 is schematically shown to be in the "off-line" position for regeneration of the catalyst. In an alternative mode of operation, both reaction zones 18 and 20 are operated in a parallel mode of operation in which they are both in service at the same time. That is, valve 16 is configured so that all of the flow from line 10 is directed to the top of reactor 18. As shown in detail in FIG. 3, the reactor 18 comprises four series connected catalyst beds designated as beds A, B, C and D. An ethylene feed stream is supplied via line 19 and proportionating valves 19a, 19b and 19c to provide for the appropriate interstage injection of ethylene. Benzene can also be introduced between the catalyst stages by means of secondary benzene supply lines 21a, 21b and 22b, respectively. As will be recognized, the parallel reactor 20 will be configured with similar manifolding as shown in FIG. 3 with respect to reactor 18.

Returning to FIG. 2, the effluent stream from the alkylation reactor 18 is supplied through a two position outlet valve 24 and outlet line 25 to a two-stage benzene recovery zone which comprises as the first stage a prefractionation column 27. Column 27 is operated to provide a light overhead fraction including benzene which is supplied via line 28 to line 15 where it is mixed with benzene from line 12 and then to the alkylation reactor input line 10. A heavier liquid fraction containing benzene, ethylbenzene and polyethylbenzene is supplied via line 30 to the second stage 32 of the benzene separation zone. Stages 27 and 32 may take the form of distillation columns of any suitable type, typically, columns having from about 20–60 trays. The overheads fraction from column 32 contains the remaining benzene which is recycled via line 34 to the alkylation reactor input. The heavier bottoms fraction from column 32 is supplied via line 36 to a secondary separation zone 38 for the recovery of monoalkylated aromatic component, e.g. ethylbenzene. The overheads fraction from column 38 comprises relatively pure ethylbenzene which is supplied to storage or to any suitable product destination by way of line 40. By way of example, the ethylbenzene may be used as a feedstream to a styrene plant in which styrene is produced by the dehydrogenation of ethylbenzene. The bottoms fraction containing polyethylbenzenes, heavier aromatics and normally only a small amount of ethylbenzene is supplied through line 41 to a tertiary polyethylbenzene separation zone 42. The bottoms fraction of column 42 comprises a residue which can be withdrawn from the process via line 44 for further use in any suitable manner. The overhead fraction from column 42 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 45 and 46 are provided through inlet and outlet connections involving valves 47 and 48. While one transalkylation reactor is on-stream, the other can be undergoing regeneration operation in order to burn coke off the catalyst beds. Alternatively, both of reactors 45 and 46 can be placed on stream at the same time so that both are in service in a parallel mode of operation. By minimizing the amount of ethylbenzene recovered from the bottom of column 38, the ethylbenzene content of the transalkylation feedstream can be kept small in order to drive the transalkylation reaction in the direction of ethylbenzene production. The polyethylbenzene fraction withdrawn overhead from column 42 through line 49 is mixed with benzene supplied via line 50 and then supplied to the on-line transalkylation reactor 45 via line 51. Preferably, the benzene feed supplied via line 50 is of relatively low water content, about 0.05 wt. % or less. Preferably, the water content is reduced to a level of about 0.02 wt. % or less and more preferably to no more than 0.01 wt. %. The transalkylation reactor is operated as described before in order to maintain the benzene and alkylated benzenes within the transalkylation reactor in the liquid phase. Typically, the alkylation reactor and transalkylation reactor may be operated to provide an average temperature within the transalkylation reactor of about 150° F.–550° F. and an average pressure of about 600 psi. The catalyst employed in the transalkylation reactor is the high porosity zeolite-Y having the characteristics described previously. The weight ratio of benzene to polyethylbenzene should be at least 1:1 and preferably is within the range of 1:1 to 4:1.

The output from the transalkylation reactor containing benzene, ethylbenzene and diminished amounts of polyethylbenzene is supplied via line 52 to the initial stage of the benzene recovery zone. This mode of operation is contrary to the normal mode of operation as disclosed in the aforementioned EPA 467,007 to Butler. As disclosed there, the output from the transalkylation reactor is supplied to the second stage of the benzene recovery zone, corresponding to column 32 in FIG. 2. While this mode of operation can be followed in carrying out the present invention, it is preferred to operate, as shown in FIG. 2, in which the transalkylation reactor output is supplied to the initial stage 27 of the benzene recovery zone. This offers the advantage of having a stream with approximately the same benzene and ethylbenzene composition as the stream from the alkylation reaction.

In the process shown schematically in FIG. 2, the entire bottoms fraction from the ethylbenzene separation column 38 is applied to the tertiary separation column 42 with overhead fractions from this zone then applied to the transalkylation reactor. This mode of operation offers the advantage of relatively long cycle lengths of the catalyst in the transalkylation reactor between regeneration of the catalyst to increase the catalyst activity. Another embodiment of the invention achieves this advantage by supplying a portion of the output from the ethylbenzene separation column directly to the transalkylation reactor. By employing vapor phase alkylation coupled with liquid phase transalkylation in accordance with the present invention, a significant quantity of the bottoms fraction from the ethylbenzene column can be sent directly to the transalkylation reactor, thus decreasing the amount of residue which is lost from the process. While applicants' invention is not to be limited by theory, it is believed that direct application of a substantial portion of the output from the ethylbenzene separation zone to the transalkylation reactor is made possible, at least in part, by the low water content in the process stream resulting from low water content introduced initially into the transalkylation reactor.

Figure 4:
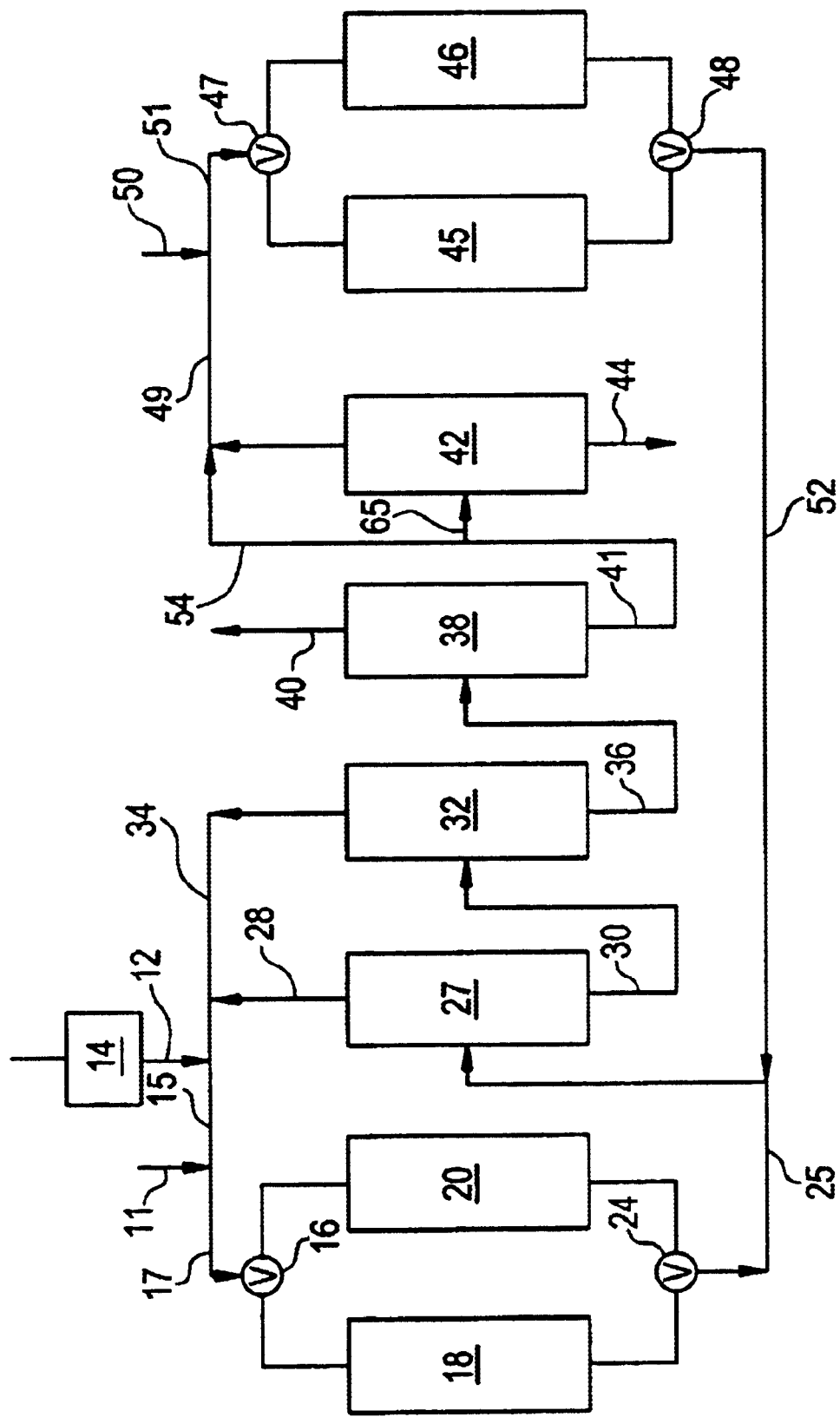
FIG. 4 is a schematic illustration of another embodiment of the invention incorporating an integrated process involving separate alkylation and transalkylation reactors and intermediate a separation and recycle systems.

This embodiment of the invention is shown in FIG. 4 in which like elements and components as are shown in FIG. 2 are illustrated by the same reference numerals as used in FIG. 2. As shown in FIG. 4, a portion of the bottoms fraction from the secondary separation zone 38 is supplied directly to the transalkylation reactor 45 via line 54. A second portion of the bottoms fraction from the ethylbenzene column is applied to the tertiary separation column 42 via line 55. The overhead fraction from column 42 is commingled with the bypass effluent in line 54 and the resulting mixture is fed to the transalkylation reactor via line 47. By bypassing the column 42 with a substantial portion of the bottoms product from column 38, the residue which is lost from the system can be reduced. In a preferred embodiment of the invention, a substantial amount of the bottoms product from column 38 is sent directly to the transalkylation reactor, bypassing the polyethylbenzene column 42. Normally, the weight ratio of the first portion supplied via line 54 directly to the transalkylation reactor to the second portion supplied initially via line 55 to the polyethylbenzene would be within the range of about 1:2 to about 2:1. However, the relative amounts may vary somewhat more widely to be within the range of a weight ratio of the first portion to the second portion in a ratio of about 1:3 to 3:1.

In a further application of the invention, the embodiment of either FIG. 2 or FIG. 4 may be coupled with a novel heat integration and heat exchange procedure in order to improve the thermal energy relationships encountered in carrying out the alkylation/transalkylation process of the present invention. Various feedstreams and recycle streams involved in the present invention are incorporated into the integrated heat exchange process as described in co-pending application Ser. No. 08/739,897 filed on Oct. 30, 1996, by James Merrill et al, entitled "Heat Integration in Alkylation/Transalkylation Process," the entire disclosure of which is incorporated herein.

In experimental work relative to the present invention, transalkylation was carried out over two types of zeolite-Y molecular sieves. One zeolite-Y denominated herein, Catalyst A, was a standard zeolite-Y molecular sieve of the type used in transalkylation reactions. This catalyst, had a normal porosity, characterized in terms of surface area, of a 625 $m^2/g$. The catalyst also had a relatively high bulk density of 39.5 lbs. per cubic foot (determined in terms of the zeolite without taking the binder into account) and a unit cell size of 24.45 angstroms. The second zeolite-Y catalyst used in the experimental work, a high porosity zeolite-Y, had a much lower surface area of 380 $m^2$ $\mu$g. This catalyst also had a bulk density of 33 lbs. per cubic foot, nearly one-fifth lower than the zeolite-Y, and had a unit cell size of 24.52 angstroms. While Applicant's invention is not to be limited by theory, it is postulated that the lower surface area, indicating a higher porosity, is also consistent with somewhat larger pores, increasing the stability of the catalyst for use in transalkylation which involves larger molecules than those involved in the alkylation reaction.

As shown by the experimental work which was carried out with polyethylbenzene feed which had not been subject to a previous transalkylation reaction (denominated "pre-transalkylation polyethylbenzene"), the high porosity zeolite-Y had an initial activity corresponding to the initial activity of the standard zeolite-Y but underwent a higher deactivation rate as measured by the reaction temperature required to a standard polyethylbenzene conversion—in this case, 65% conversion of diethylbenzene. This is consistent with greater infusion of the polyethylbenzene, which had not been previously subjected to transalkylation, into the catalyst pores. In similar experimental work carried out using polyethylbenzene feed which had previously been subjected to a transalkylation reaction, denominated post-transalkylation PEB feed," the high porosity zeolite-Y catalyst showed the same or a slightly lower deactivation rate over the early part of the test run and further showed a more or less leveling out with time to a point at which further deactivation did not appear to occur.

In this experimental work the transalkylation work was carried out in a liquid phase reactor operated in an upflow mode under a pressure of 500 psig. The polyethylbenzene feed was supplied at a liquid hourly space velocity (LSHV) of 12 $hrs^{-1}$ and blended with benzene to provide 15 wt. % DEB in the feed.

Figure 5:
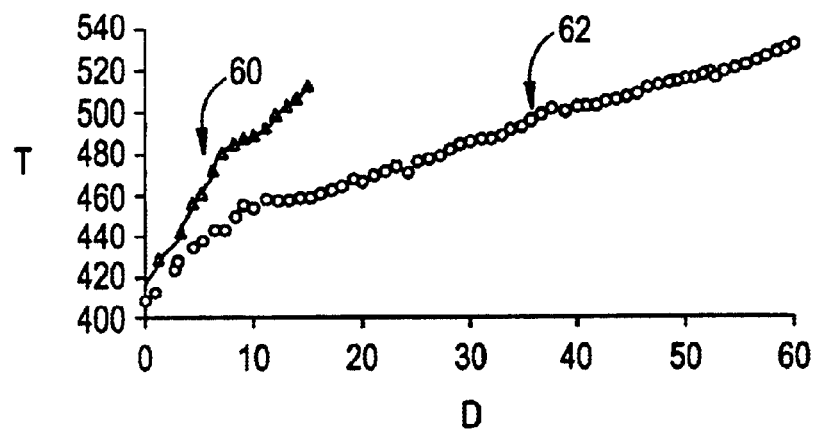
FIG. 5 is a graphical presentation showing the results of the experimental work carried out with a polyethylbenzene feedstream which has not been previously subjected to transalkylation over a normal zeolite-Y catalyst and a high porosity zeolite-Y catalyst of the type used in the present to invention.
Figure 6:
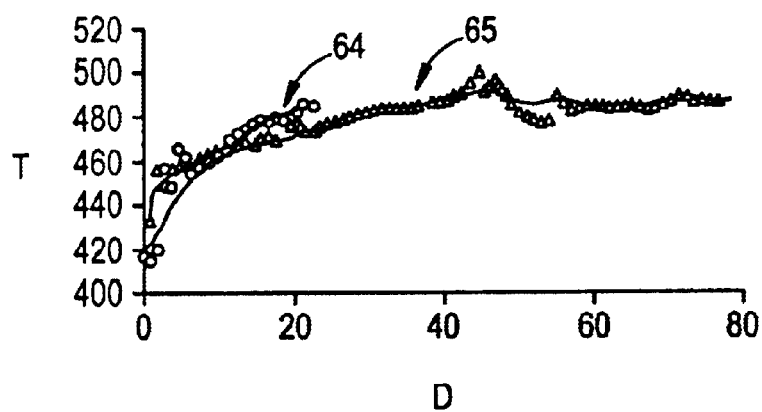
FIG. 6 is a graphical illustrating of experimental work carried out employing a high porosity zeolite-Y catalyst and a normal zeolite-Y catalyst in the transalkylation of a post-transalkylation polyethylbenzene feedstream.

The results of this experimental work are presented in FIGS. 5 and 6 in which the temperature T, in degrees F, required to achieve 65 wt. % diethylbenzene conversion is plotted on the ordinate versus duration of the run, D, in days on the abscissa. In FIG. 5, the activity plot for the high porosity zeolite-Y indicated by curve 60, and the conversion rate for the standard zeolite-Y catalyst is shown by curve 62. As indicated previously, the temperature required to maintain 65% diethylbenzene conversion rose rapidly for 15 days, at which time the test run was terminated. The temperature required for the standard DEB conversion using the standard zeolite-Y transalkylation catalyst rose relatively rapidly during the first ten days and then continued to increase at a somewhat lower rate in almost a straight line relationship.

FIG. 6 illustrates the results achieved employing the high porosity zeolite-Y as compared with the normal zeolite-Y when employing post-transalkylation polyethylbenzene. As will be recognized by those skilled in the art, the test runs with the post-transalkylation polyethylbenzene are consistent with the integrated process operation in which output from the transalkylation reactor is recycled as described previously. In FIG. 6, curve 64, indicated by the data points ● shows the temperature required for 65% DEB conversion for the standard zeolite-Y. The corresponding data for the high porosity zeolite-Y used in the present invention is indicated by curve 65 (shown by the data points Δ).

Figure 7:
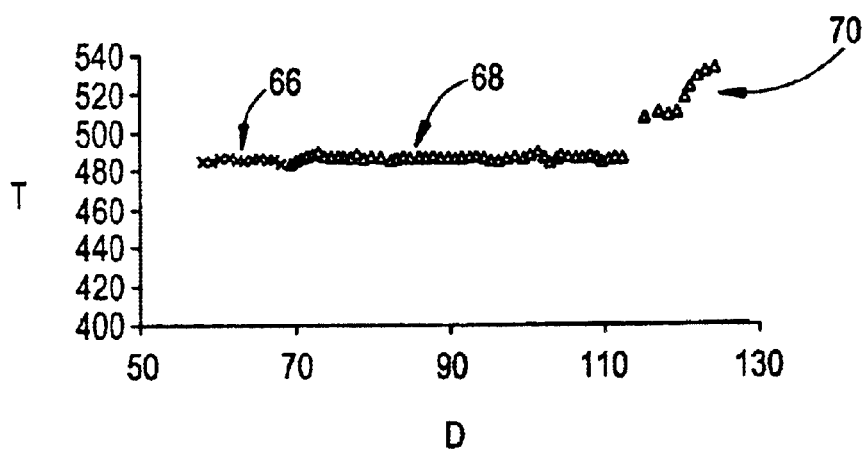
FIG. 7 is a graphical presentation showing the stability of a high porosity zeolite-Y catalyst of the type employed in the present invention over prolonged periods of time.

The stability of the post-transalkylation polyethylbenzene over the high porosity zeolite-Y catalyst is confirmed by further experimental work shown in FIG. 7. In FIG. 7 the temperature T in degrees F. is plotted on the ordinate versus the time, D, in days on stream for the test run on the abscissa for a polyethylbenzene fraction recovered from a fractionation column employed in actual plant operations corresponding generally to the column 42 shown in FIG. 2. The curve 66 shows the temperature required to achieve 65% DEB conversion, and curve 68 shows the temperature required to achieve 70% DEB conversion. As can be seen from an examination of FIG. 7, the catalyst remained completely stable over the time interval ranging from 58 day to about 112 days. At the conclusion of the test carried out with the polyethylbenzene overheads fraction, the same catalyst was used to effect transalkylation of a bottoms fraction from a feed column producing the polyethylbenzene in the overhead, corresponding generally to the bottoms fraction from column 38 in FIG. 2. Here, deactivation progressively increased for a period of about 10 days at a rate of 2° F. per day as shown by curve 70. It will be recognized that the feedstream used in the test run indicated by curve 70 contained substantially higher molecular weight aromatic compounds than the feedstreams used in attaining the results shown by curves 66 and 68.

The advantages of using the high porosity zeolite-Y as a transalkylation catalyst in accordance with the present invention involving recycle of the transalkylation output are readily apparent from the foregoing experimental work. After a relatively-short initial period, the high porosity zeolite-Y remains very stable over prolonged periods of time with the post-transalkylated zeolite-Y. The post-transalkylated polyethylbenzene feed can be expected to contain a complex mixture of polyethylbenzene resulting from the previous pass of the alkylated aromatic compounds through the transalkylation reactor. The high porosity zeolite-Y would appear to provide enhanced access to the catalyst site within the molecular sieve structure, resulting in improved stability over time for the high porosity catalyst.

Having described specific embodiments of the invention, it will be understood that modifications thereof may be suggested to those skilled in the art, and it is intended to cover all such modifications as fall within the scope of the appended claims.

What is claimed:

1. In alkylation and transalkylation of aromatic compounds, a process comprising:
    (a) supplying a feedstock containing benzene into a multistage alkylation reaction zone having a plurality of series connected catalyst beds each containing a molecular sieve aromatic alkylation catalyst having a pore size which is smaller than the average pore size of the hereinafter-recited zeolite-Y wherein said alkylation catalyst comprises predominately monoclinic silicalite having a crystal size of $0.5\mu$ or less and formulated with an alumina binder to provide catalyst particles having a surface are/volume ratio of at least 60 $in^{-1}$;
    (b) supplying ethylene to said reaction zone;
    (c) operating said reaction zone at temperature and pressure conditions to maintain said feedstock in the gaseous phase and causing gas-phase alkylation of said benzene by said ethylene in the presence of said catalyst to produce an alkylated product comprising a mixture of monoalkylated and polyalkylated aromatic components;
    (d) recovering said alkylated product from said reaction zone and supplying said product from said reaction zone to a benzene recovery zone for the separation of benzene substrate from said alkylated product;
    (e) operating said benzene recovery zone to produce a lower boiling benzene containing fraction and a higher boiling fraction comprising a mixture of monoalkylated aromatic and polyalkylated aromatic component;
    (f) recycling benzene from said benzene recovery zone to said reaction zone;
    (g) supplying said higher boiling fraction from said benzene recovery zone to a secondary separation zone;
    (h) operating said secondary separation zone to produce a secondary lower boiling fraction comprising a monoalkylated aromatic component and a higher boiling fraction comprising a heavier polyalkylated aromatic component;
    (i) supplying at least a portion of said polyalkylated aromatic component including the dialkylated and trialkylated aromatics in said polyalkylated component to a transalkylation reaction zone containing a high porosity zeolite-Y molecular sieve having a surface area of no more than 500 $m^2/g$;
    (j) supplying benzene to said transalkylation zone;
    (k) operating said transalkylation reaction zone under temperature and pressure conditions to maintain said benzene in the liquid phase and effective to cause disproportionation of said polyalkylated aromatic fraction to arrive at a disproportionation product having a reduced polyalkyl benzene content and an enhanced monoalkyl benzene content;
    (l) supplying at least a portion of said disproportionation product to said benzene recovery zone.

2. The method of claim 1 wherein at least some of said heavier polyalkylated aromatic component from said secondary separation zone is, prior to operation of paragraph (i), applied to a tertiary separation zone wherein said heavier polyalkylated aromatic component is separated into a tertiary lower boiling fraction of said polyalkylated aromatic component comprising dialkyl and trialkyl aromatics and a heavier higher boiling residue fraction and wherein said tertiary lower boiling fraction of said polyalkylated aromatic component is supplied to said transalkylation reaction zone in accordance with paragraph (i).

3. The method of claim 2 wherein a first portion of the heavier polyalkylated aromatic component is supplied to said tertiary separation zone in accordance with claim 2 and thence from said tertiary separation zone to said transalkylation zone and a second portion of said heavier polyalkylated aromatic component from said secondary separation zone is supplied directly to said transalkylation zone.

4. The method of claim 3 wherein said high porosity zeolite-Y molecular sieve has a surface area of about 400 $m^2/g$ or less.

* * * * *

UNITED STATES PATENT AND TRADEMARK OFFICE
CERTIFICATE OF CORRECTION

PATENT NO. : 6,897,346 B1
DATED : May 24, 2005
INVENTOR(S) : James T. Merrill and James R. Butler It is certified that error appears in the above-identified patent and that said Letters Patent is hereby corrected as shown below:

Column 1,
Line 39, replace "sane" with -- same --;
Line 67, after "below," insert -- it is often the practice to --;

Column 2,
Line 30, replace "400°14 475° C." with -- 400°-475° C. --;
Line 53, replace "temperature" with -- temperatures --;

Column 3,
Line 22, replace "to Ward et al" with -- to Wight --;
Line 25, replace "alklylation" with -- alkylation --;

Column 6,
Line 50, remove "As" prior to "Normally";
Line 54, replace "stages of if" with -- stages of --;

Column 8,
Line 55, remove "GNU" prior to "mole ratio";

Column 11,
Line 63, after "of a" add -- surface area of --;

Column 12,
Line 2, replace "m2 ug" with -- m2/g --;
Line 40, replace "versus duration" with -- versus the duration --; and
Line 42, replace "zeolite-Y indicated" with -- zeolite-Y is indicated --.

Signed and Sealed this

Seventeenth Day of January, 2006

JON W. DUDAS
*Director of the United States Patent and Trademark Office*